(12) United States Patent
Hess

(10) Patent No.: US 8,663,239 B2
(45) Date of Patent: Mar. 4, 2014

(54) TISSUE REMOVAL AND MANIPULATOR DEVICE FOR LAVH AND RELATED SURGERIES

(76) Inventor: Blake Hess, Glendale, AZ (US)

(*) Notice: Subject to any disclaimer, the term of this patent is extended or adjusted under 35 U.S.C. 154(b) by 15 days.

(21) Appl. No.: 13/248,194

(22) Filed: Sep. 29, 2011

(65) Prior Publication Data
US 2013/0085508 A1   Apr. 4, 2013

(51) Int. Cl.
*A61B 17/42* (2006.01)

(52) U.S. Cl.
USPC .................................. 606/119; 606/193

(58) Field of Classification Search
USPC ................... 606/119, 193, 108, 185; 604/164.01–170.03
See application file for complete search history.

(56) References Cited

U.S. PATENT DOCUMENTS

| | | | |
|---|---|---|---|
| 3,796,214 A | 3/1974 | Davis | |
| 5,209,754 A | 5/1993 | Ahluwalia | |
| 5,394,863 A | 3/1995 | Stanford et al. | |
| 5,928,249 A | 7/1999 | Saadat et al. | |
| 5,951,465 A | 9/1999 | Sxhiff et al. | |
| 2003/0097122 A1* | 5/2003 | Ganz et al. | 606/7 |
| 2010/0305578 A1* | 12/2010 | Auerbach et al. | 606/119 |
| 2012/0143209 A1* | 6/2012 | Brecheen et al. | 606/119 |

FOREIGN PATENT DOCUMENTS

| | | | |
|---|---|---|---|
| DE | 19543576 | 6/1997 | |
| EP | 0871403 | 1/2003 | |
| WO | 9621392 | 7/1996 | |
| WO | 9718757 | 5/1997 | |
| WO | WO 2010/098905 | * 9/2010 | A61M 5/178 |

* cited by examiner

*Primary Examiner* — Thomas McEvoy
(74) *Attorney, Agent, or Firm* — Venable, Campillo, Logan & Meaney PC

(57) ABSTRACT

The invention is incorporated into a tissue removal and manipulation device for vaginal hysterectomies and related surgeries. The present invention solves the suturing problem of the prior art devices by providing a device that not only can manipulate the uterus during surgery but remove the uterus without the need for suturing.

14 Claims, 5 Drawing Sheets

TISSUE REMOVAL AND MANIPULATOR DEVICE FOR LAVH AND RELATED SURGERIES

BACKGROUND OF THE INVENTION

1. Field of the Invention

The present invention relates to a surgical device for use in connection with vaginal related surgeries, and more specifically to a surgical device for use in connection with a vaginal hysterectomy.

2. Discussion of the Related Art

The surgical field is always searching for ways to improve patient outcome. A few of the common ways to improve patient outcome include: (1) employing techniques that shorten the length of surgery, (2) employing techniques that make the surgery less traumatic on the patient, and (3) employing techniques that do both.

A hysterectomy is the surgical removal of the uterus and is the second most common type of major surgery performed on women of childbearing age. Advances in laparoscopic surgical equipment have enabled surgeons to remove the uterus and/or ovaries laparoscopically. While the advantages of a laparoscopic hysterectomy or a laparoscopically assisted vaginal hysterectomy (LAVH) are well-known, a considerable amount of surgical time is spent securing sutures to the uterus for the purpose of removing the uterus at a later stage. This time lengthens the surgery and increases trauma on the patient as a result of the lengthened surgery. What is needed is a uterine manipulator that improves patient outcome by reducing surgical time and patient trauma by eliminating the need for suturing the uterus in order to facilitate later removal.

A number of devices have been developed to improve vaginal hysterectomy and related procedures. Prior devices have been disclosed in the following United States patents: U.S. Pat. No. 5,951,465 (Schiff et al), U.S. Pat. No. 5,394,863 (Stanford, et al), U.S. Pat. No. 3,796,214 (Davis), U.S. Pat. No. 5,928,249 (Saadat et al.), and U.S. Pat. No. 5,209,754 (Ahluwalia). None, however, disclose the aspects of this present invention.

SUMMARY OF THE INVENTION

The invention is summarized below only for purposes of introducing embodiments of the invention. The ultimate scope of the invention is to be limited only to the claims that follow the specification.

Generally, the present invention is incorporated into a tissue removal and manipulation device for vaginal hysterectomies and related surgeries. The present invention solves the suturing problem of the prior art devices by providing a device that not only can manipulate the uterus during surgery but can remove the uterus without the need for suturing.

The present invention is incorporated in a device 10 for the manipulation of the uterus that includes an elongated shaft 20, a retractable barb 30, a cervical cup 40, and an expandable balloon 50. The retractable barb 30 is located close enough to the distal end 22 of the device 10 so that after completing the colpotomy stage of a hysterectomy, the retractable barb 30 can be deployed inside the uterus. Once deployed inside the uterus, the cervix can be compressed between the retractable barbs 30 and the cervical cup 40 prior to removal of the device 10. Thus, when device 10 is removed post-colpotomy, the compression on the cervix enables the uterus to be removed as one unit with the device 10.

To use device 10, the following steps are preferred: (1) dilate the cervix to fit the distal end 22 of device 10; (2) introduce the distal end 22 of device 10 to the uterus so that the retractable barb 30 passes the cervix; (3) expand the balloon 50 inside the uterus to provide some resistance against the cervix, (4) slide the cervical cup 40 down over the cervix and secure cup 40 with the anti-backslide collar 52 to keep the cervical cup 40 pressed against the cervix to aid in manipulating the uterus as needed during surgery, (5) activate the circumferential illuminator to locate fornix and assist with surgical colpotomy, (6) (post-colpotomy) deploy barbs 30 and retract elongated shaft while keeping cervical cup 40 over the cervix in order to secure uterus to device 10, and (7) remove the device 10 with the uterus as one unit.

It is an object of the invention to eliminate the cervix suturing step for hysterectomy surgeries and related surgeries by replacing the suturing step with at least one retractable barb 30 in order to remove the uterus.

It is an object of the invention to use a retractable barb to make it easier, less traumatic, and quicker to extract the uterus during a hysterectomy surgery.

It is an object of the invention to give a surgeon a visual guide to colpotomy for laparoscopic hysterectomy.

It is an object of the invention to make colpotomy more accurate and to make it easier to recognize the tissue to be cut.

DESCRIPTION OF THE DRAWINGS OF PREFERRED EMBODIMENT

Figure 10A:
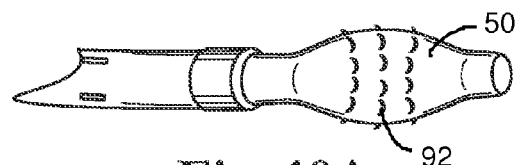
FIG. 10A illustrates another embodiment of the expandable balloon 50.
Figure 10B:
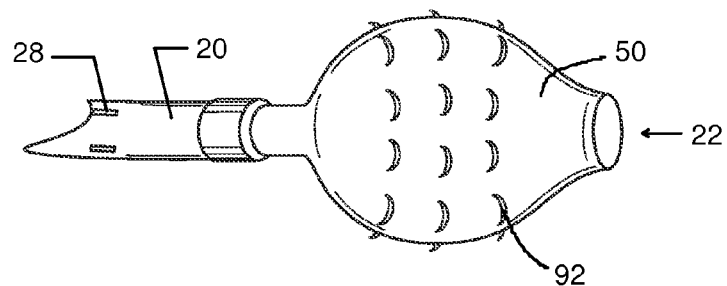
FIG. 10B illustrates the expandable balloon 50 of FIG. 10A in an expanded position.
Figure 10C:
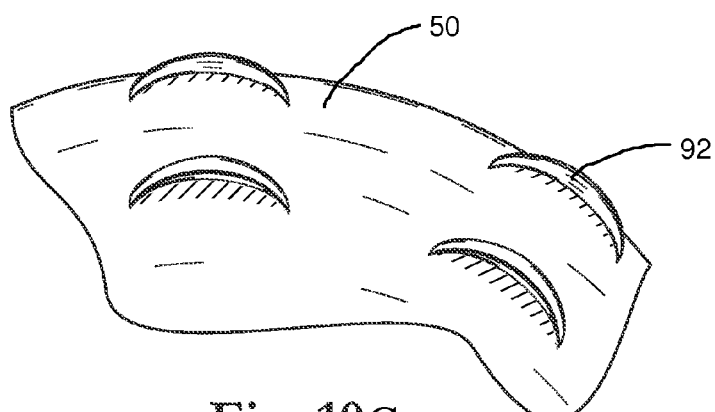

FIG. 10C an isometric view of a paddle scoop embodiment.

DESCRIPTION OF PREFERRED EMBODIMENT

The descriptions below are merely illustrative of the presently preferred embodiments of the invention and no limitations are intended to the detail of construction or design herein shown other than as defined in the appended claims.

The present invention is incorporated in a device 10 for the manipulation of the uterus that preferably includes an elongated shaft 20, a retractable barb 30, and a cervical cup 40. Most preferably, the device 10 includes a plurality of retractable barbs 30, an illuminable ring 42, an expandable balloon 50 and an anti-backslide collar 52. An overview of the preferred steps is as follows: the cervix is dilated to fit the distal end 22 of device 10; the distal end 22 of device 10 is introduced to the uterus so that the retractable barb 30 passes through to the inside of the cervix; the balloon 50 is expanded the uterus to provide some resistance against the cervix; the cervical cup 40 is moved down onto the cervix and the cervical cup 40 is secured against back-sliding with the anti-backslide collar 52 to keep the cervical cup 40 pressed against the cervix; the circumferential illuminator is turned on to assist in locating the fornix and assist with surgical colpotomy; post-colpotomy, the barbs 30 are deployed while keeping cervical cup 40 over the cervix compressing the cervix between the cup 40 and the barbs 30 in order to secure uterus to device 10; and the device 10 is removed with the uterus as one unit.

Figure 1:
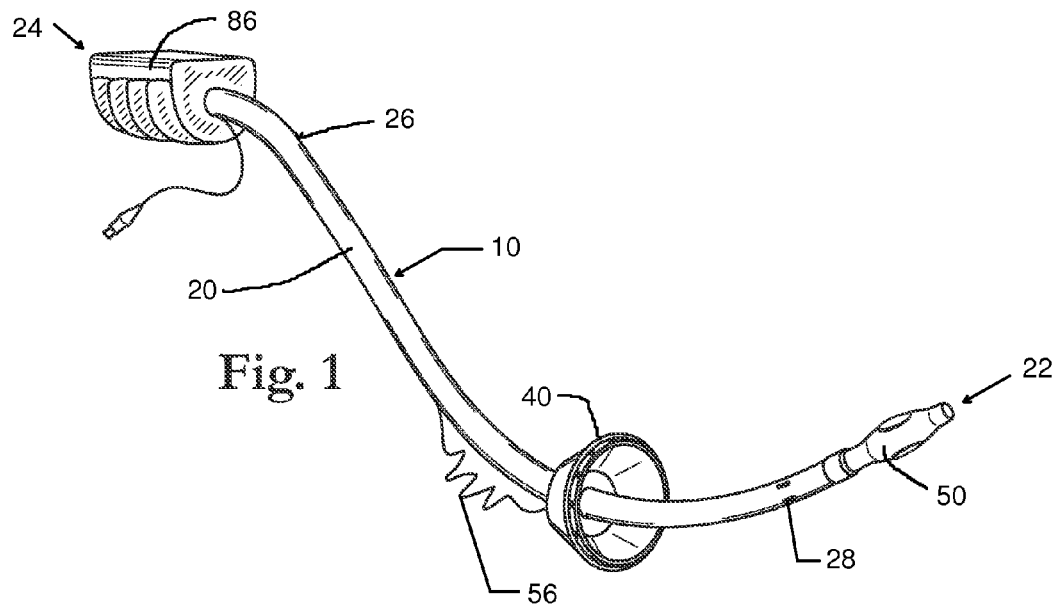
FIG. 1 illustrates perspective view of a basic embodiment of the device 10.

More specifically, as shown in FIG. 1, the elongated shaft 20 has a distal end 22, a proximal end 24 and an outer surface 26. The preferred elongated shaft 20 houses a central shaft 80 as shown in FIGS. 6A-7B and discussed in more detail below. The elongated shaft 20 has a plurality of holes to permit the tissue-hooking segment 34 of a retractable barb 30 to protrude.

Figure 6A:
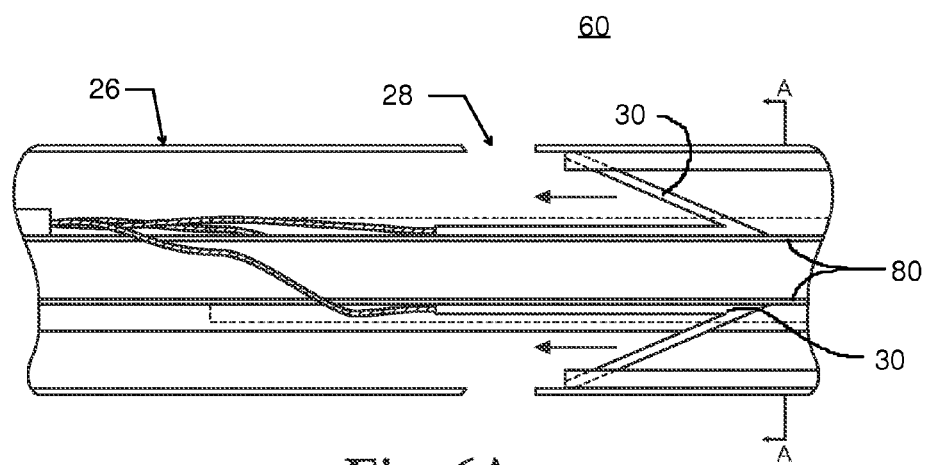
FIG. 6A illustrates a cut view of the elongated shaft at the barb location with the barbs in the first position 60 (not deployed).
Figure 6B:
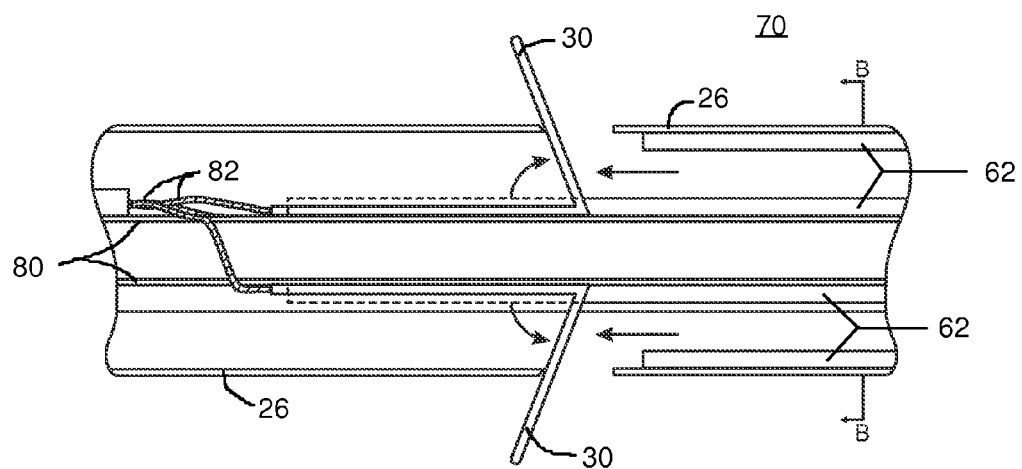
FIG. 6B illustrates a cut view of the elongated shaft at the barb location with the barbs in the second position 70 (deployed).

While at least one retractable barb 30 is required, it is preferable to have a plurality of retractable barbs 30. FIGS. 6A and 6B illustrate the presently preferred embodiment of four retractable barbs 30. As illustrated, the preferred retractable barbs 30 should have at least two positions: a first position 60 where the barb 30 is flush or below with the outer surface 26 of the elongated shaft 20, and a second position 70 where the barb 30 projects beyond the outer surface 26 of the shaft 20.

FIG. 6A shows the retractable barbs 30 in the first position 60 (or the retracted position). As shown in FIG. 6A, the retractable barb 30 is completely inside the elongated shaft 20 and below its outer surface 26. FIG. 6B shows the retractable barbs 20 in the second position 70 (or the deployed position). As shown in FIG. 6B, the retractable barbs 30 extend beyond the outer surface 26 of the elongated shaft 20.

Figures 7A, 7B:
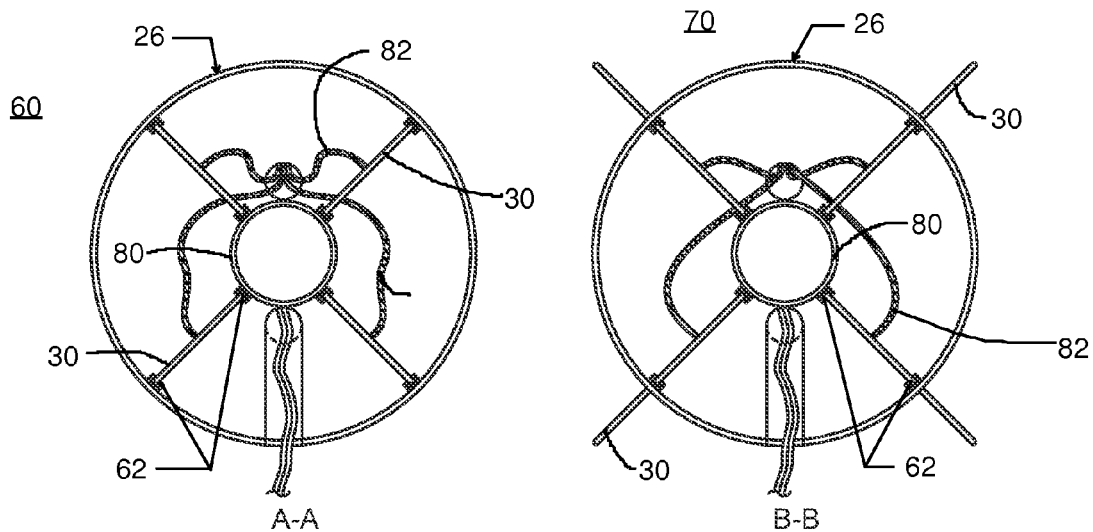
FIG. 7A illustrates cut A-A from FIG. 6A with the barbs in the first position (not deployed).
FIG. 7B illustrates cut B-B from FIG. 6B with the barbs in the second position (deployed).

Turning to FIGS. 7A and 7B, it is preferred that each retractable barb 30 slide lengthwise within the elongated shaft 20. While there are a variety of ways to accomplish this, it is presently preferred that the retractable barbs 30 slide in opposing slots 62, located in the space between the outside of central shaft 80 and the inside surface of the elongated shaft 20. The slots 62 can be created by securing a length of channel to the inner and outer walls respectively as shown in FIGS. 6A-7B.

FIGS. 6A-7B also illustrate the preferred embodiment of the interior of the elongated shaft 20. In addition to the central shaft 80, a pull-able cord 82 is also housed inside the elongated shaft 20. The cord 82 can be made from a variety of suitable materials known in the art like cotton, metal, nylon or similar flexible tension-bearing material. One end of the cord 82 is accessible to the user at the proximal end 24 of the device 10. The other end of cord 82 is connected to a barb 30. While the connection can be achieved in a variety of ways, the preferred connection is to thread cord 82 a through a hole 32 and tying it off.

Figure 8:
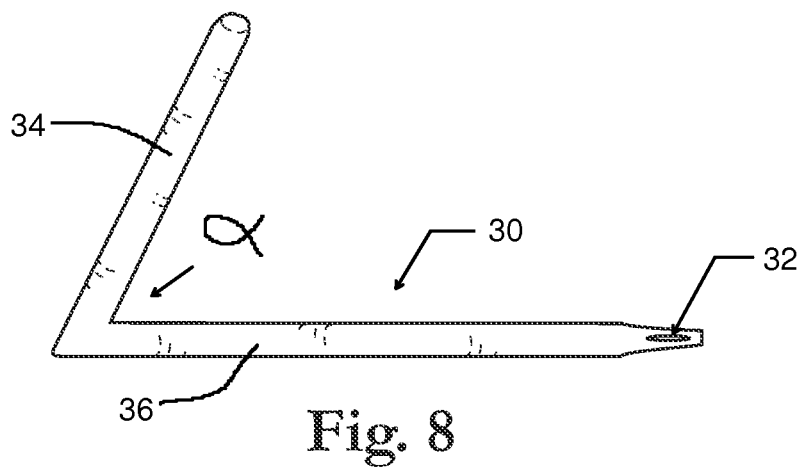
FIG. 8 illustrates an embodiment of the retractable barb 30
Figure 9A:
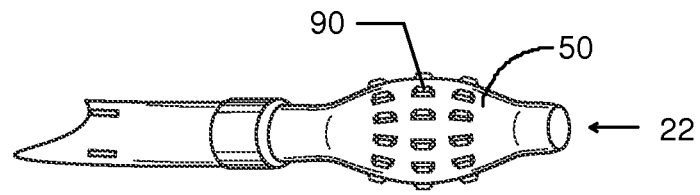
FIG. 9A illustrates an embodiment of the expandable balloon 50.
Figure 9B:
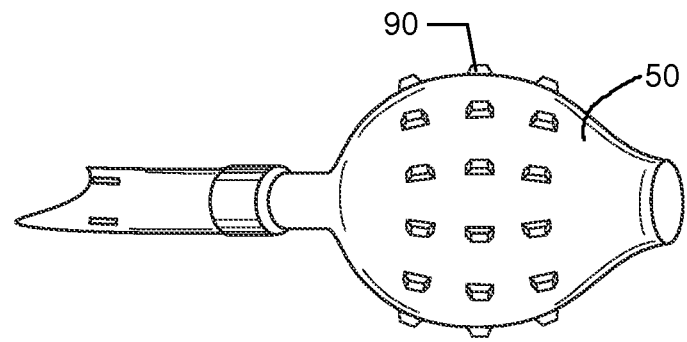
FIG. 9B illustrates the expandable balloon 50 of FIG. 9A in an expanded position.
Figure 9C:
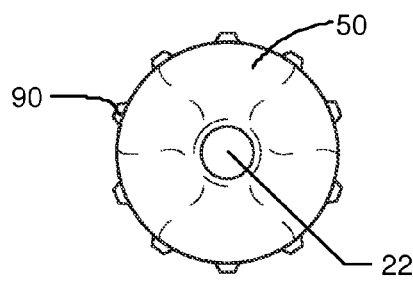
FIG. 9C illustrates an end view of FIG. 9A.

FIG. 8 illustrates the preferred embodiment of the barb 20. The preferred barb 30 is a piece of metal bent back upon itself to create a tissue-hooking segment 34 and a shaft-sliding segment 36, the shaft-sliding segment 36 having hole 32 for securing cord 82. The stiffness of the metal and the partial bend impart a spring characteristic on the tissue-hooking segment 34. In the first position 60, the tissue-hooking segment 34 is forward of barb-deployment portal 28 on elongated shaft 20. The wall of the elongated shaft 20 prevents the tissue-hooking segment 34 from springing outward and deploying prematurely.

After the colpotomy is complete the tissue-hooking segment 34 is deployed by pulling on the cord 82, preferably using a deployment ring 84 on a handle 86. Pulling on the ring 84 slides the retractable barb 30 along the opposing slots 62 in the direction of the proximal end 24. When the tissue hooking segment 34 reaches the barb-deployment portal 28, the tissue-hooking segment 34 springs outward and extends through the portal 28 into the second position 70. Inside the handle in line with the cable is a cord clamp 88 that prevents the barb 30 from retracting.

As shown in FIG. 6B, in the second position 70, the tissue-hooking segment 34 extends beyond the outer surface 26 of the elongated shaft 20 and forms an acute angle α with shaft-sliding segment 36. Because the tissue-hooking segment 34 will be angled toward the cervix in the second position 70, the tissue-hooking segment 34, once deployed, will engage the inner orifice of the cervix as the device 10 is removed from the uterus.

A cervical cup 40, preferably in the shape of a hollow truncated cone, is shown in FIGS. 1-4. The preferred cervical cup 40 has an open top and a closed bottom with a bottom cup hole 44 through which the elongated shaft 20 can be slidably inserted through. The cervical cup 40 is oriented on the elongate shaft to oppose the barb when the barb is in the second position 70.

Figure 2:
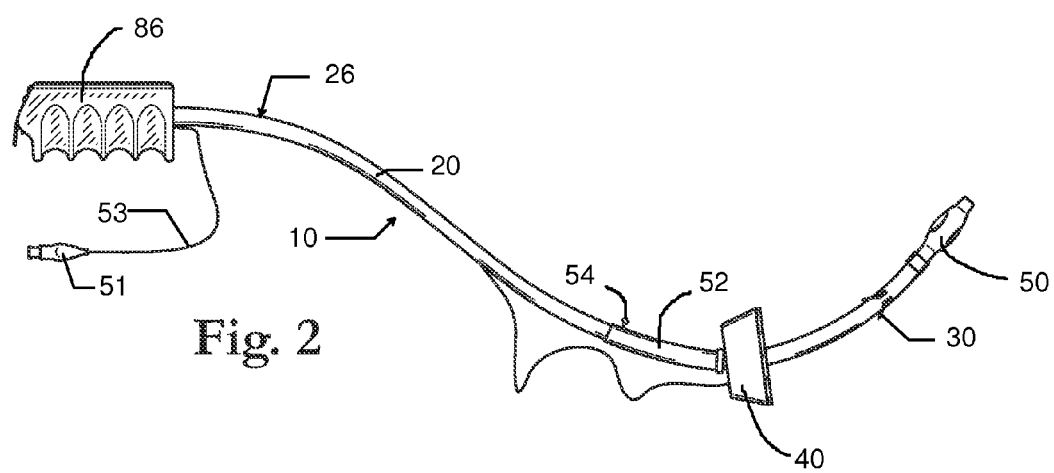
FIG. 2 illustrates a side view of a basic embodiment of the device 10.

Also shown in FIGS. 1-2 is an anti-backslide collar 52. The purpose of anti-backslide collar 52 is to keep the cervical cup from backsliding on the elongated shaft 20 (i.e., sliding toward the proximal end 24) once the cervical cup 40 is placed on the cervix. The anti-backslide collar 52 can be made in a variety of ways. It is preferred to make anti-backslide collar 52 from a sleeve of hard plastic so it can slide on the elongated shaft 20. It is also preferred to that the anti-backslide collar 52 have a set screw 54 to set the collar relative to the elongated shaft once the cervical cup 40 is in position on the cervix.

Figure 3:
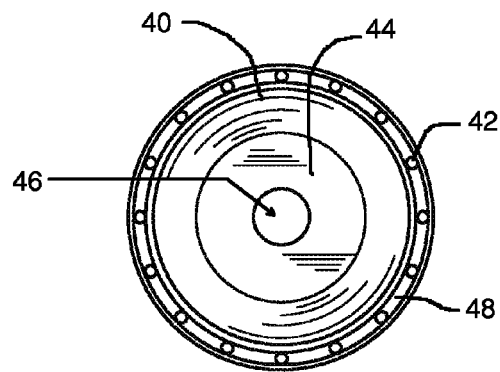
FIG. 3 illustrates a front view of the cervical cup 40.
Figure 4:
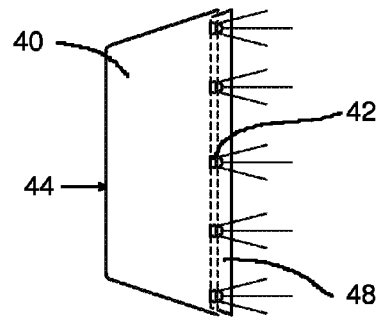
FIG. 4 illustrates a side view of the cervical cup 40 with the circumference of the open end illuminated with led lights.
Figure 5A:
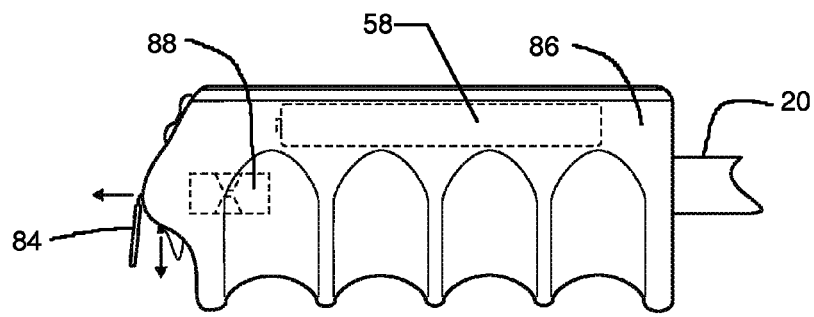
FIG. 5A illustrates a side view the preferred embodiment of the handle and the pull string to deploy the barb.
Figure 5B:
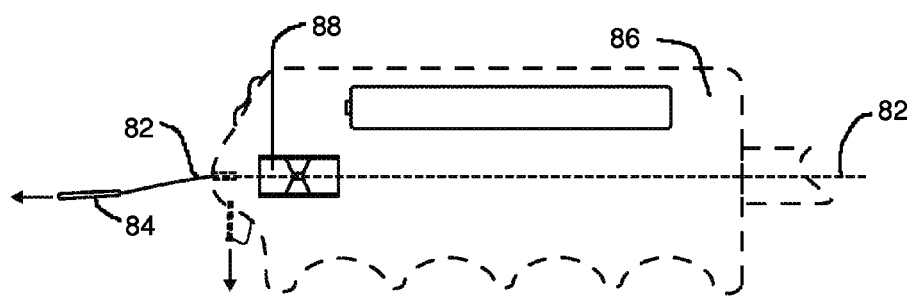
FIG. 5B illustrates a side interior view of the preferred embodiment of the handle and the pull string moving the barb 20 into the deployed position.

As shown in FIGS. 3 and 4, it is preferred that at least the circumferential rim 48 of the open top of the cervical cup 40 be capable of illumination. Illumination can be accomplished by embedding LED lights around the circumference of the open top and connecting the lights to an energy source, such as battery 58, via cable 56. Other ways to illuminate the circumferential ring, such as fiber optics, are known in the art and can be suitable.

The purpose of illuminating the circumferential rim 48 is to eliminate the need for the surgeon to estimate where the fornix is located by feel or pressure from the cervical cup 40. An illuminated circumferential rim 48 creates a halo effect that will show through tissue, such as around the fornix when the cervical cup 40 is engaged with the cervix at its fornix. The halo effect will show through and illuminate the fornix viewed from the interior of the uterus, laparoscopically or otherwise. This will enable the surgeon to cut desired tissue more efficiently and more accurately.

Another preferred option is to include a balloon on the distal end 22 of the elongated shaft 20. Attaching a balloon to the distal end 22 of the elongated shaft is known in the art. See, e.g., U.S. Pat. No. 5,209,754 (Ahluwalia) at 2:55-3:17. Although there are many ways to make the expandable balloon element, it is presently preferred to inflate using air or saline from a syringe, a supply line 53 and a one-way valve 51 (e.g., a luer-type valve). The supply line 53 can run from from the syringe to the balloon 50 through the elongated shaft 20 or the central shaft 80.

What was not known prior to this invention, however, is to attach a balloon not having a smooth surface. A balloon with a smooth surface can sometimes slip during manipulation. For this invention, it is preferred to use a balloon having a non-smooth surface in order to better engage the inner wall of the uterus. Most preferably the balloon 50 has molded knobs 90 or raised sections 92 that emerge when the balloon 50 is inflated as shown in FIGS. 9A-10C. The knobs 90 or raised sections 92 of the balloon engage the inner wall of the uterus to counter-act slippage. While the knobs 90 or raised sections 92 can take a variety of shapes, the preferred shape of the raised section 92 is a "paddle scoop" shape as oriented and shown in FIGS. 10A-C.

In operation, the following steps are preferred:
a. Dilate the cervix to fit the distal end 22 of device 10;
b. Introduce the distal end 22 of device 10 to the uterus so that the retractable barb 30 passes the cervix;
c. Inflate the expandable balloon 50;
d. Slide the cervical cup 40 down over the cervix and secure the cup with the anti-backslide collar 52;
e. Activate the circumferential illuminator to locate fornix and assist surgical procedure;
f. Complete colpotomy;
g. Deploy barbs 30;
h. With barbs 30 deployed, which keeps cervical cup 40 over the cervix in order to secure uterus to device 10, retract elongated shaft 20; and,
i. Remove the device 10 with the uterus as one unit.

While the device of the present invention has been described in connection with a particular type of surgical procedure, it should be understood that this instrument may be used in other situations where deliberate directing, movement and visualization of the uterus is required. Additionally, it is understood that various changes can be made by one possessing ordinary skill in the art which would be beyond the scope of protection. Although the invention has been described in detail with reference to one or more particular preferred embodiments, persons possessing ordinary skill in the art to which this invention pertains will appreciate that various modifications and enhancements may be made without departing from the spirit and scope of the claims that follow.

What is claimed is:

1. A device for the manipulation of the uterus comprising:
an elongated shaft having a distal end, a proximal end and an outer surface;
a plurality of barbs located on the elongated shaft, the barbs having at least two positions: a first position where the barbs are below the outer surface of the elongated shaft, and a second position where the barbs project beyond the outer surface of the shaft;
a cervical cup slidably connected to the elongated shaft via a hole in a bottom of the cervical cup; an open end of the cervical cup being oriented on the elongated shaft to oppose the barbs when the barbs are in the second position; and
an expandable balloon connected to the distal end of the elongated shaft,
wherein during use of the device, the cervical cup is placed on the outside of the cervix, opposing the barbs when the barbs are in the second position to engage the uterus and remove the uterus when the device is removed; and
the cervical cup is illuminated via LED light.

2. The device according to claim 1 wherein the illumination occurs along a rim of the top portion of the cup.

3. The device according to claim 1, further comprising an anti-backslide collar slidably connected to the elongated shaft.

4. The device according to claim 1, wherein the expandable balloon comprises knobs on the outside surface.

5. The device according to claim 4, wherein the knobs are in the shape of paddle scoops.

6. The device according to claim 1, the barbs each comprising two segments, a tissue-hooking segment and a shaft sliding segment, wherein the tissue-hooking segment and the shaft sliding segment are separated by an acute angle when in the second position.

7. A device for the manipulation of the uterus comprising:
an elongated shaft having a distal end, a proximal end and an outer surface;
a plurality of barbs located on the elongated shaft, the barbs having at least two positions: a first position where the barbs are below the outer surface of the elongated shaft, and a second position where the barbs project beyond the outer surface of the shaft after the barbs are moved along a longitudinal direction of the shaft from the first position;
a cervical cup slidably connected to the elongated shaft via a hole in a bottom of the cervical cup; an open end of the cervical cup being oriented on the elongated shaft to oppose the barbs when the barbs are in the second position; and
an expandable balloon connected to the distal end of the elongated shaft,
wherein during use of the device, the cervical cup is placed on the outside of the cervix, opposing the barbs when the barbs are in the second position to engage the uterus and remove the uterus when the device is removed; and
the cervical cup is illuminated via LED light.

8. The device according to claim 7 wherein the illumination occurs along a rim of the top portion of the cup.

9. The device according to claim 7, further comprising an anti-backslide collar slidably connected to the elongated shaft.

10. The device according to claim 7, wherein the expandable balloon comprises knobs on the outside surface.

11. The device according to claim 10, wherein the knobs are in the shape of paddle scoops.

12. The device according to claim 7, the barbs each comprising two segments, a tissue-hooking segment and a shaft sliding segment, wherein the tissue-hooking segment and the shaft sliding segment are separated by an acute angle when in the second position.

13. A device for the manipulation of the uterus comprising:
an elongated shaft having a distal end, a proximal end and an outer surface;
a plurality of barbs located on the elongated shaft, the barbs having at least two positions: a first position where the barbs are below the outer surface of the elongated shaft, and a second position where the barbs project beyond the outer surface of the shaft after the barbs rotate relative to the shaft about an axis perpendicular to a longitudinal direction of the shaft from the first position;
a cervical cup slidably connected to the elongated shaft via a hole in a bottom of the cervical cup; an open end of the cervical cup being oriented on the elongated shaft to oppose the barbs when the barbs are in the second position; and
an expandable balloon connected to the distal end of the elongated shaft, wherein during use of the device, the cervical cup is placed on the outside of the cervix, opposing the barbs when the barbs are in the second position to engage the uterus and remove the uterus when the device is removed; and the cervical cup is illuminated via LED light.

14. The device according to claim 13, further comprising an anti-backslide collar slidably connected to the elongated shaft.

\* \* \* \* \*